US006501003B1

(12) United States Patent
Messing et al.

(10) Patent No.: US 6,501,003 B1
(45) Date of Patent: Dec. 31, 2002

(54) TRANSGENTIC MOUSE EXPRESSING GREEN FLUORESCENT PROTEIN IN GLIAL CELLS

(75) Inventors: Albee Messing, Madison, WI (US); Lang Zhuo, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/111,667

(22) Filed: Jul. 8, 1998

(51) Int. Cl.$^7$ .......................... A61K 67/00; G01N 33/00

(52) U.S. Cl. ............................................ 800/18; 800/3

(58) Field of Search ................................ 800/3, 14, 18

(56) References Cited

U.S. PATENT DOCUMENTS

| | | |
|---|---|---|
| 4,873,191 | 10/1989 | Wagner et al. ............ 435/172.3 |
| 5,614,396 | 3/1997 | Bradley et al. ........... 435/172.3 |
| 5,627,047 | 5/1997 | Brenner et al. ............. 435/69.1 |
| 5,654,183 | 8/1997 | Anderson et al. ........ 435/172.3 |
| 5,667,968 | 9/1997 | La Vail et al. ................. 514/12 |

FOREIGN PATENT DOCUMENTS

| | | |
|---|---|---|
| WO | WO93/07280 | 4/1993 |
| WO | WO94/17208 | 8/1994 |

OTHER PUBLICATIONS

Felsenstein et al. Alzheimer's and Parkinson's Disease, Hanin, I., Ed., Plenum Press NY, pp. 401–409, 1995.*
Oster–Granite et al. J. Neuroscience, vol. 16, pp. 6732–6741, 1996.*
Okabe et al., "Green Mice" as a source of ubiquitous green cells, 1997, FEBS Letters, vol. 407, pp. 313–319.*
Ikawa et al., Green fluorescent protein as a marker in transgenic mice, 1995, Develop. Growth Differ., vol. 37, pp. 455–459.*
Brenner et al., GFAP promoter directs astrocyte–specific expression in transgenic mice, 1994, The Journal of Neuroscience, vol. 14, No. 3, pp. 1030–1037.*
Brenner et al., GFAP transgenic mice, 1996, Methods: A Companion to Methods in Enzymology, vol. 10, pp. 351–364.*
Ebert, K.M. et al. A Moloney MLV–Rat Somatotropin Fusion Gene Produces Biologically Active Somatotropin in a Transgenic Pig. Molecular Endocrinology 2:277–283, 1988.*
Hammer, R.E. et al. Genetic Engineering of Mammalian Embryos. Journal of Animal Science 63:269–278, 1986.*
Mullins, L.J. et al. Perspective Series: Molecular Medicine in Genetically Engineered Animals. Journal of Clinical Investigations 98(11):S37–S40, 1996.*

O'Callaghan, J.P. Biochemcial Analysis of Glial Fibrillary Acidic Protein as a Quantitative Approach to Neurotoxicity Assessment: Advantages, Disadvantages and Application to the Assessment of NMDA Receptor Antagonist–Induced Neurotoxicity. Psychopharmacology Bulletin 30:549–554, 1994.*
Strojek, R.M. The Use of Trangenic Animal Techniques for Livestock Development. Genetic Engineering: Principles and Methods 10:221–246, 1988.*
Wall, R.J. Transgenic Livestock: Progress and Prospects for the Future. Theriogenology 45:57–68, 1996.*
Zhuo, L. et al. Live Astrocytes Visualized by Green Fluorescent Protein in Transgenic Mice. Developmental Biology 187(1):36–42, Jul. 1997.*
Database PubMed, US National Library of Medicine, (Bethesda, MD, USA), No. 97367905, Zhou et al., "Live astrocytes visualized by green fluorescent protein in transgenic mice," abstract, Dev. Biol. Jul. 1, 1997.*
Galou, M., et al., "Normal and Pathological Expression of GFAP Promoter Elements in Transgenic Mice", GLIA, 12: 281–293 (1994).
Ikawa, M., et al., "Green mice'and their potential usage in biological research", FEBS letters, vol. 430, No. 1–2 pp. 83–87 (1998).
Toews et al., "Primary Demyelination Induced by Exposure to Tellurium Alters Schwann Cell Gene Expression: A Model for Intracellular Targeting of NGF Receptor", Journal of Neuroscience 12(9): 3676–3687 (Sep. 1992).
Wu, Vivian W., and Joan P. Schwartz, "Cell Culture Models for Reactive Gliosis: New Perspectives", J. Neurosci. Res. 51: 675–681 (1998)—published sufficiently before filing date such that month is not an issue
Verderber et al., "Differential Regulation of a Glial Fibrillary Acidic Protein–LacZ Transgene in Retinal Astrocytes and Müller Cells", Invest. Ophthalmol. Vis. Sci., 36(6): 1137–1143 (May 1995).
O'Callaghan, James P., "Biochemical Analysis of Glial Fibrillary Acidic Protein as a Quantitative Approach to Neurotoxicity Assessment: Advantages, Disadvantages and Application to the Assessment of NMDA Receptor Antagonist–Induced Neurotoxicity", Psychopharmacology Bulletin 30(4): 549–554 (1994)—published sufficiently before filing date such that month is not an issue.
Cavanagh et al., "Clinical and Diagnostic Use of In Vivo Confocal Microscopy in Patients with Corneal Disease", Ophthalomology 100(10): 1444–1454 (Oct. 1993).

(List continued on next page.)

Primary Examiner—Michael C. Wilson
(74) Attorney, Agent, or Firm—Michael Best & Friedrich LLP; Teresa J. Welch

(57) ABSTRACT

A transgenic mammal, specifically a mouse, containing in its genome a humanized mutant of green fluorescent protein operably linked to the glial fibrillary acidic protein promoter is provided. The mouse can be used to assay the effects of systemic or topical administration of neurotoxins and also to assay the effects of physical damage to neural tissue.

3 Claims, 11 Drawing Sheets

OTHER PUBLICATIONS

Muldoon et al., "Tracking and Quantitation of Retroviral-Mediated Transfer Using a Completely Humanized, Red-Shifted Green Flourescent Protein Gene", BioTechniques 22(1): 162–167 (Jan. 1997).

Mucke et al., "Rapid Activation of Astrocyte-Specific Expression of GFAP-lacZ Transgene by Focal Injury", The New Biologist 3(5): 465–474 (May 1991).

Zhuo et al., "Live Astrocytes Visualized by Green Fluorescent Protein in Transgenic Mice", Developmental Biology 187(1) 36–42 (Jul. 1997).

Rutka et al., "Role of Glial Filaments in Cells and Tumors of Glial Origin: A Review", J. Neurosurg. 87: 420–430 (Sep. 1997).

Mancardi et al., "Schwann Cell GFAP Expression Increases in Axonal Neuropathies", J. Neurological Sciences 102: 177–183 (1991)—published sufficiently before filing date such that month is not an issue.

Baba et al., "GFAP Gene Expression During Development of Astrocyte", Dev. Neurosci. 19: 49–57 (1997)—published sufficiently before filing date such that month is not an issue.

O'Callaghan, James P., "Quantification of Glial Fibrillary Acidic Protein: Comparison of Slot-Immunobinding Assays With a Novel Sandwich ELISA", Neurotoxicol. Teratol. 13: 275–281 (1991)—published sufficiently before filing date such that month is not an issue.

* cited by examiner

Northern blot of the tg94 lines

Non-tg   Tg94.4   Tg94.5   Tg94.7   Tg94.8

1.3kb

SEQUENCE LISTING

<160> NUMBER OF SEQ ID NOS: 10

<210> SEQ ID NO 1
<211> LENGTH: 19
<212> TYPE: DNA
<213> ORGANISM: Homo sapiens

<400> SEQUENCE: 1
ctctagagtc gacggatcc

-continued

```
<210> SEQ ID NO 2
<211> LENGTH: 21
<212> TYPE: DNA
<213> ORGANISM: Mus musculus

<400> SEQUENCE: 2
gatccgcaga tcccggccag a                                              21

<210> SEQ ID NO 3
<211> LENGTH: 21
<212> TYPE: DNA
<213> ORGANISM: Aequorea victoria

<400> SEQUENCE: 3
agcttgccgc caccatggtg a                                              21

<210> SEQ ID NO 4
<211> LENGTH: 22
<212> TYPE: DNA
<213> ORGANISM: Aequorea victoria

<400> SEQUENCE: 4
agtaaagcgg ccgcgactct ag                                             22

<210> SEQ ID NO 5
<211> LENGTH: 27
<212> TYPE: DNA
<213> ORGANISM: Aequorea victoria

<400> SEQUENCE: 5
cccgtcgcca ccatggtgag caagggc                                        27

<210> SEQ ID NO 6
<211> LENGTH: 18
<212> TYPE: DNA
<213> ORGANISM: Aequorea victoria

<400> SEQUENCE: 6
tacaagtaaa gcgggcgc                                                  18

<210> SEQ ID NO 7
<211> LENGTH: 27
<212> TYPE: DNA
<213> ORGANISM: Aequorea victoria

<400> SEQUENCE: 7
ccggtcgcca ccatggtgag caagggc                                        27

<210> SEQ ID NO 8
<211> LENGTH: 21
<212> TYPE: DNA
<213> ORGANISM: Aequorea victoria

<400> SEQUENCE: 8
ctgtacaagt aaagcggccg c                                              21

<210> SEQ ID NO 9
<211> LENGTH: 20
<212> TYPE: DNA
<213> ORGANISM: Homo sapiens

<400> SEQUENCE: 9
actccttcat aaagccctcg                                                20
```

```
<210> SEQ ID NO 10
<211> LENGTH: 20
<212> TYPE: DNA
<213> ORGANISM: Artificial Sequence
<220> FEATURE:
<223> OTHER INFORMATION: Humanized nucleotide sequence designed based
      on coding sequence for green fluorescent protein using codons
      recognized in humans

<400> SEQUENCE: 10
aagtcgatgc ccttcagctc                                                   20
```

TRANSGENTIC MOUSE EXPRESSING GREEN FLUORESCENT PROTEIN IN GLIAL CELLS

This invention was made with United States government support awarded by the following agencies: NIH, Grant Nos: NS-22475; NS23375; RR00094. The United States has certain rights in this invention.

FIELD OF THE INVENTION

The present invention is related to a transgenic mouse expressing green fluorescent protein under the control of a human glial fibrillary protein promoter and to a method of determining the neurotoxicity of substances in vivo.

BACKGROUND OF THE INVENTION

Neural tissue consists of neurons and supporting or glial cells. Glial cells outnumber neurons by about ten to one in the mammalian brain. Glial cells may be divided into four classes: astrocytes, oligodendrocytes, ependymal cells and microligal cells. Astrocytes descend from a primitive neuroepithelial stem cell line within the ependymal zone. The exact function of astrocytes is unknown. Astrocytes probably provide support for the delicate neurons, contribute to the synthesis and degradation of neurotransmitters, control the ionic environment of the neurons and provide spacing between neurons.

Glial fibrillary acidic protein (GFAP) is expressed primarily in astrocytes of the central nervous system (including Mueller cells of the retina and non-myelinating Schwann cells of the peripheral nervous system). GFAP is a 50 kD intracytoplasmic protein that is the primary intermediate filament in the cytoskeleton of astrocytes. Mouse and human GFAP genomic genes have been cloned and sequenced as described in U.S. Pat. No. 5,267,047, incorporated herein by reference. The GFAP gene contains a basal promoter consisting of a TATA box and a CAAT box. Several enhancer and silencer sequences have also been identified. The enhancers for GFAP expression are found between −250 and −80 bp and between −1980 and −1500 bp. These positive control regions contain consensus sequences for many transcription factors including a cAMP response element and binding sites for the Sp-1, NF-1, AP-1 and AP-2 transcription factors. Tissue specificity is conferred by a human GFAP consensus sequence (hgcs) located in the −1980 to −1500 bp region. The transactivating protein which binds to this site has not been identified.

Reactive gliosis (also known as astrogliosis) occurs in response to almost any insult, physical or chemical, to the central nervous system (CNS). Reactive gliosis is characterized by hypertrophy of the astrocyte cell body and its processes, accompanied by an increase in expression of GFAP. One of the major problems in neurotoxicity screening is the diversity of insults that are to be tested and the highly specific nature of their targets, particularly for the pharmacological agents that may affect very discrete populations of neurons. Reactive gliosis in glial cells, in which up-regulation of GFAP is an invariant part, represents a robust change in the central nervous system following injuries to all of the relevant cell types in the central nervous system (neurons, oligodendrocytes, vascular elements, and astrocytes themselves). In the peripheral nervous system, a similar increase in GFAP occurs following both traumatic and toxic injuries tp peripheral nerve [(Mancardi et al., J.Neurosci. 102, 177 (1991); Toews et al., J.Neurosci. 12, 3676 (1992); Quattrini et al., Glia 17, 294 (1996)]. In frogs, peri-synaptic Schwann cells at the neuromuscular junction also respond to degeneration of the nerve terminals by forming sprouts and increasing expression of GFAP.

The correlation between the upregulation of GFAP expression and neural injury has been recognized as providing a possible biochemical indicator of neurotoxic or physical damage to the CNS. (See Mucke, *The New Biologist*, Vol. 3, No. 5, 465 (May 1991); O'Callaghan, *Neurotoxicology and Teratology*, Vol. 13, 275 (1991); O'Callaghan, *Psychopharmacology Bulletin* 30, 549 (1994); Verderber et al., *Invest. Ophthalmol. Visual Sci.* 36, 1137 (1995); and Wu et al., *J.Neurosci. Res.* 51, 675 (1998).) Mice transgenic for a GFAP-lacZ transgene exhibit increased production of the fusion protein in astrocytes of physically damaged brain and retina neural tissue. Likewise, exposure of mice to chemical neurotoxins results in increased wild-type GFAP expression as measured by immunohistochemistry and ELISA assays. Reactive gliosis in response to neurotoxin challenge is dose-, time-, and region-dependent. ELISA assays indicate that gliosis occurs at toxicant levels below those that cause light microscopic evidence of cell loss or damage.

The green fluorescent protein (GFP), a single peptide of 238 amino acids derived from the jellyfish *Aequorea victoria*, absorbs blue light and emits green light without a requirement for any cofactor or substrate. After the formation of its fluorophore by endogenous posttranslational cyclization, GFP is quite stable and remains fluorescent even after the harsh treatments found in many biochemical assays, such as 1% sodium dodecyl sulphate (SDS), 4% formaldehyde, and incubation at 65° C. Since the first report of its use in *Escherichia coli* and *Caenorhabditis elegans* by Chalfie et al., *Science* 263, 802 (1994), GFP has found many applications as a reporter gene in a number of higher organisms including Drosophila [Wang et al., *Nature* 369, 400 (1994)] and zebrafish [Amsterdam et al., *Dev. Biol.* 171, 123 (1995); Peters et al., *Dev. Biol.* 171, 252 (1995)].

The versatility of the GFP is enhanced by its ability to remain fluorescent as a fusion protein allowing studies of the subcellular distribution and dynamics of various proteins, including NMDA receptors [Marshall et al., *Neuron* 14, 211 (1995); Niswender et al., *J. Microsc.* 180, 109 (1995); Aoki et al., *FEBS Lett.* 384, 193 (1996)]. Recently, a "humanized" version of GFP has become available in which silent mutations were introduced to alter the codons to those more commonly used in mammals. The "humanized" GFP is generally expressed at higher levels in mammalian systems than wild-type GFP. Mutant forms of GFP have become available which emit light of greater intensity or which exhibit wavelength shifts. (See Clontech Catalogue, 1998).

These genetically altered proteins offer increased sensitivity in assays for measuring neural insult. They offer an opportunity to assess the toxicity of substances at much lower levels than heretofore possible with conventional approaches. For example, WO94/17208 discloses a method of assessing toxicity by independent measurement of the expression of four different types of stress promoters. Detection of increased levels of stress gene expression is effected either by nucleic acid hybridization or a reporter gene such as the genes encoding glutathione transferase, luciferase, chloramphenicol acetyl transferase, or galactose kinase.

Another conventional approach is the use of cell cultures in studying gliosis, as reviewed recently by Wu, et al., supra. Astrocytes were cultured or co-cultured with other cell types under a variety of conditions to establish a baseline under one or more biochemical or morphological parameters, and then the baselines compared to cells subjected to various damaging sources of stress. Glial markers include GFAP, vimentin and trophic factor.

SUMMARY OF THE INVENTION

Over the past several years considerable effort has gone into the development of non-invasive imaging techniques for studies of tissue structure, metabolism, and most recently, gene expression. Non-invasive imaging in neurotoxicity screening would offer particular benefits in that testing would not require sacrifice of the animal, thereby reducing costs and improving animal welfare. Scientifically, a major advantage would be the possibility of repeat measurements on the same animal over time, to assess longer term effects of potentially toxic substances.

Accordingly, it is an object of the present invention to provide an assay system free of the artifacts of tissue culture. It is also an object of the present invention to provide assays for physical and neurotoxic challenges to the nervous system, more sensitive to low dose toxicants than conventional methods. It is a still further object to provide a non-invasive assay of neurologic toxicity capable of monitoring toxic effects over a period of time on more than one occasion in the same animal.

The present invention provides a rodent, preferably a mouse, which expresses a transgene encoding a humanized fluorescent green protein gene operably linked to a glial fibrillary acidic protein promoter. In this mouse the fluorescent green protein is upregulated specifically in glial cells such as astrocytes, Schwann cells, and Mueller cells in response to neural insult of a chemical or physical nature in which neural degeneration is manifest. The usefulness of the mouse lies in the ability to assay upregulation of the fluorescent green gene by visualizing fluorescence with a confocal microscope directly from the retina or cornea. The retinal site is a non-invasive locus for study of systemic toxicity. The cornea is particularly well suited to assessing toxicity of substances applied directly to an organ containing glial cells without invading the body.

The mouse is engineered by insertion of a genetic construct into the pronucleus (preferably the male pronucleus) of a mammalian zygote, and allowing stable genomic integration to occur naturally. The zygote is then transferred to a receptive uterus, and allowed to develop to term. While the mouse is a preferred species, rats and rabbits are also potential candidates for pronuclear insertion. The genetic construct which renders the zygote transgenic comprises a full length glial fibrillary acidic protein promoter to provide glial cell specific expression. The promoter is located 5' of and operably linked to a mutant gene encoding fluorescent green protein, and a segment of DNA located 3' of the mutant fluorescent green protein encoding gene containing signal sequences for proper RNA splicing and polyadenylation.

More specifically, the genetic construct contains DNA sequences in 5' to 3' order as follows: a glial fibrillary acidic protein promoter having at its 3' end a sequence corresponding to SEQ ID NO: 1, a fluorescent reporter gene operably linked 3' thereto, and polyadenylation signal sequence linked 3' of the reporter gene. The fluorescent reporter gene is preferably hGFP-S65T green fluorescent protein gene, EGFP-1 green fluorescent gene, or EYFP-1 green fluorescent protein gene, or any variant thereof having mammalian compatible or humanized sequences (e.g. codon modification which renders the construct more compatible with mammalian ribosome translation) and a mutation increasing its light emission coefficient.

In preferred embodiments, the genetic construct of the present invention has at the 3' end of the hGFP-S65T gene a joining sequence (joining the green gene and the polyadenylation signal containing sequence) corresponding to SEQ ID NO: 2 and has at its 5' end a sequence (joining the promoter to the reporter gene) a bridging sequence corresponding to SEQ ID NO: 3.

The genetic construct is further characterized in having junctions between the 5' to 3' array of genetic elements, comprising a first junctional nucleic acid sequence at the 3' end of the glial fibrillary acidic protein promoter linked to a second junctional sequence at the 5' end of the humanized fluorescent reporter gene, together with a third junctional sequence at the 3' end of the humanized fluorescent reporter gene intersecting and linked to a fourth junctional sequence at the 5' end of a polyadenylation sequence, wherein the first junctional sequence is contiguous with the second junction sequence, and the third and fourth junctional sequences are thereby contiguous to each other.

In the method of the present invention, a mouse is provided which expresses the constructs disclosed hereinabove, exposing the mouse to a substance suspected of neurotoxicity and visualizing the presence of green fluorescence signal in glial cells such as astrocytes, Mueller cells, or Schwann cells to confirm upregulation of the glial fibrillary acidic protein promoter responsive to cellular degeneration associated with chemical or physical insult. In a quantitative assay of great sensitivity, the fluorescence signal in a predetermined area of exposure and visualization is calculated as the average pixel intensity for the area, and then the fluorescence signal is compared to a control fluorescence signal obtained from a control transgenic mouse not exposed to the target or test substance.

Confocal microscopy of the retinal Mueller cells of a live mouse or the Schwann cells of the cornea can be monitored by training the laser beam onto the desired region, and detecting the level of green fluorescence emitted. In this way the above objects of the invention may be realized in obtained sensitive toxicological data of either systemically or topically administered substances without invasive procedures. The assay can be performed sequentially many times on the same animal.

DETAILED DESCRIPTION OF THE PREFERRED EMBODIMENT

Figure 1A:
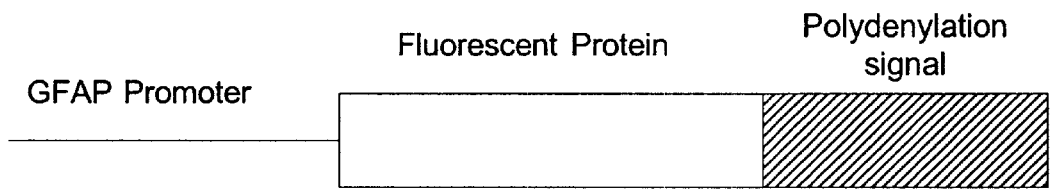
FIG. 1(A) is a graphic depiction of the GFAP transgene.

Regulatory elements within a 2.2-kb 5' flanking region of the human glial fibrillary acidic protein gene (GFAP) that were capable of directing astrocyte-specific expression of the bacterial lacZ reporter gene in vivo have been previously identified. However, standard techniques for detecting lacZ expression generally involve fixation, while fluorescent substrates for use in live cells are cumbersome and expensive [Nolan et al., *Proc. Natl. Acad. Sci. USA* 85, 2603 (1988); Zhang et al., *FASEB J.* 5, 3108 (1991)]. In a search for simpler and noninvasive methods for identifying astrocytes in situ, applicants have generated transgenic mice expressing a mutant form of GFP under the control of the human GFAP promoter [Brenner et al., *J. Neurosci.* 14, 1030 (1994)]. The utility of wild-type GFP in transgenic mice is limited by a relatively weak signal and diffusion of the GFP to neighboring cells [Ikawa et al., *Dev. Growth Differ.* 37, 455 (1995)]. Here applicants demonstrate that the transgene product hGFP-S65T effectively labels target cells in vivo, is a more reliable reporter for certain subsets of astrocytes than is lacZ, and will now allow studies of dynamic changes in gene expression and morphology in living glia.

Applicants have found that the humanized S65T mutant form of GFP, when expressed in transgenic mice under the control of the human GFAP promoter, efficiently labels astrocytes throughout the central nervous system. The intensity of the fluorescent signal, and the simplicity of the assay system (observation with standard fluorescein fluorescence optics), make GFP the reporter gene of choice for many experimental purposes. The initial characterization of the human GFAP promoter in mice utilized the bacterial lacZ gene as a reporter (Brenner et al., supra). Expression of the lacZ transgene was developmentally regulated and increased following traumatic injuries to the brain that involve gliosis and upregulation of the GFAP promoter. With minor variations, these findings were consistent with both the human and murine GFAP promoters [for review, see Brenner et al., *Methods: Companion Methods Enzymol.* 10, 351 (1996)]. However, one cell type that was known to express GFAP under certain conditions was the retinal Mueller cell, and yet none of the lacZ transgenics described have displayed expression of the reporter genes in this cell type (Brenner et al., 1994, supra; Verderber et al., supra), leading to the suggestion that Mueller cells may require regulatory elements for appropriate expression beyond those contained in the 2.2-kb 5' region, and sufficient for other astrocytic cells. In the GFAP-GFP transgenic mice described here, applicants found bright fluorescence of the GFP reporter in retinal Mueller cells when the mice were homozygous for rd, causing reactive changes in retinal glia. In addition, preliminary studies also indicate expression in peripheral nerve with a distribution consistent with nonmyelinating Schwann cells, another GFAP-expressing cell type that was unreliably labeled in lacZ transgenics [Zhuo et al., *Dev. Biol.* 187, 36 (1997) unpublished observations]. These differences suggest either that GFP is a more sensitive reporter gene than is lacZ or that other features of the lacZ sequences somehow interfere with expression in certain cell types. GFP fluorescence clearly distinguished between the nonreactive and the reactive states of retinal Mueller cells.

The genetic construct of the present invention includes, in order from 5' to 3' in plasmid Gfa2, a GFAP promoter, a humanized fluorescent protein gene, and a mouse protamine 1 intron and polyadenylation signal. The fluorescent protein gene of the present invention may be the hGFP-S65T green fluorescent protein gene derived from the plasmid whose sequence is disclosed in GenBank Accession Number U43284, herein incorporated by reference, or the pEGFP-1 green fluorescent protein gene or pEYFP-1 fluorescent protein gene, the sequences of which are disclosed in the Clontech catalog (CLONTECH Laboratories, 1020 East Meadow Circle, Palo Alto Calif., 94303). Examples of these vectors are graphically depicted in FIGS. 1A, B, and C.

The genetic construct may also be characterized as comprising functional domains A, B, C and D wherein A corresponds to DNA encoding the GFAP promoter, B corresponds to DNA encoding a fluorescent protein gene, C corresponds to DNA encoding the mouse protamine 1 intron and D corresponds to DNA encoding the mouse protamine 1 polyadenylation signal sequence. Each of these elements may be joined in a 5' to 3' orientation by methods well known in the art as described in Maniatis et al., Molecular Cloning, Cold Spring Harbor Laboratory Press, herein incorporated by reference.

The GFAP promoter and mouse protamine intron and polyadenylation signal were derived from the plasmid Gfa2-lac2. The sequence of Gfa2-lac2 is disclosed in Brenner et al., 1994, incorporated herein by reference. The sequence encoding lacZ was removed from plasmid Gfa2-lac1 by BamH1 digestion. The digested plasmid was then prepared for blunt end ligation by filling in overhangs by incubation with Klenow fragment. At this stage, the digested plasmid contained the GFAP promoter, which had at its 3' end a blunt ended junctional sequence corresponding to SEQ ID NO: 1. The digested plasmid also contained the mouse protamine 1 intron and polyadenylation signal, which has at its 5' end a blunt ended junctional sequence corresponding to SEQ ID NO: 2.

Figure 1B:
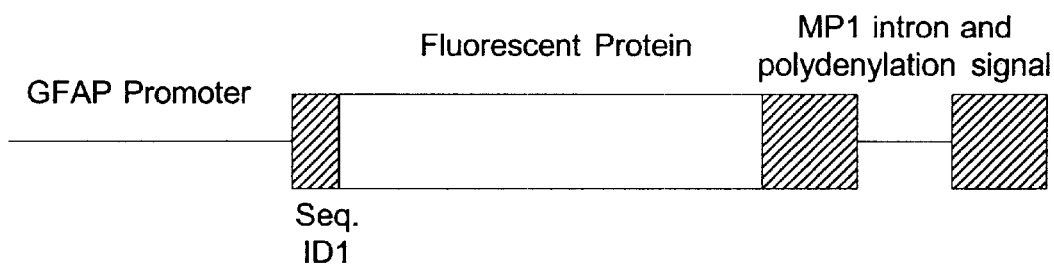
FIG. 1(B) is a graphic depiction of the GFAP transgene including the junction sequence of the GFAP promoter.
Figure 1C:
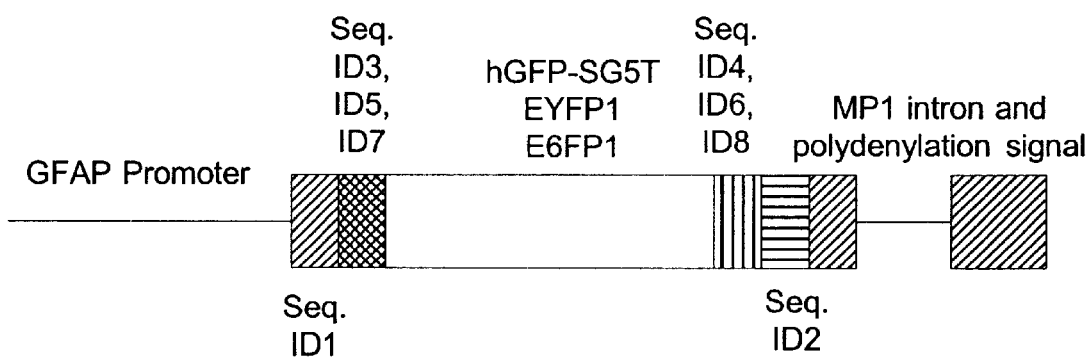
FIG. 1(C) is a graphic depiction of alternate transgenes containing different fluorescent protein genes.
Figure 1D:
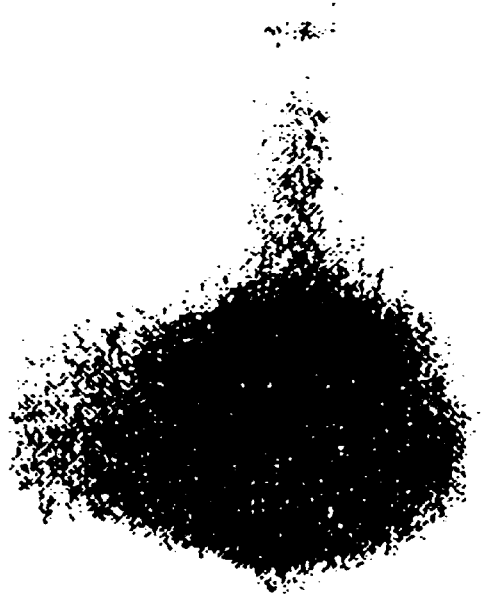
FIG. 1(D) is a northern blot demonstrating transgene expression.
Figure 1D:

The vector used for making the transgenic mouse was constructed by removing a gene encoding a humanized green fluorescent protein, hGFP-S65T, from the plasmid phGFP-S65T (CLONTECH Laboratories, Palo Alto, Calif.) by digestion of the plasmid with HindIII and Xbal. The sticky ends of the excised hGFP-S65T gene were filled in with Klenow polymerase to form a blunt ended fragment having at its 5' end a junctional sequence corresponding to SEQ ID NO. 3 and at its 3' end a junctional sequence corresponding to SEQ ID NO. 4. This fragment was then inserted into the digested, blunt end plasmid Gfa2 by blunt end ligation to form a plasmid in which the junctional sequence corresponding to SEQ ID NO: 1 is contiguous with the junctional sequence corresponding to SEQ ID NO: 3 and in which the junctional sequence corresponding to SEQ ID NO: 4 is contiguous with the junctional sequence corresponding to SEQ ID NO: 2 as shown in FIG. 1C. The vector which was injected into the mouse zygote was then prepared by digesting the ligated plasmid with BglII.

It will be understood by those skilled in the art that vectors containing alternative fluorescent protein genes may be constructed as described above. For instance, a vector may be constructed using the fluorescent protein genes contained in the plasmids pEGFP-1 and pEGYP1 (CLONTECH Laboratories, Palo Alto, Calif.). The EGFP-1 gene may be excised from the pEGFP-1 plasmid by digesting the plasmid with Age1 and Not1. The overhangs may then be filled in by blunt end ligation to yield the EGFP1 gene having at its 5' end the junctional sequence corresponding to SEQ ID NO. 5 and having at its 3' end the junctional sequence corresponding to SEQ ID NO: 6. This fragment may then be inserted into the digested, blunt end plasmid Gfa2 by blunt end ligation to form a plasmid in which the DNA encoding SEQ ID NO: 1 is contiguous with the DNA encoding SEQ ID NO: 5 and in which the DNA encoding SEQ ID NO: 6 is contiguous with the DNA encoding SEQ ID NO: 2 as shown in FIG. 1C. A vector for injection into a mouse zygote may then be prepared by digesting the ligated plasmid with a suitable restriction enzyme.

Likewise, the EYFP-1 gene may be excised from the pEYFP-1 plasmid by digesting the plasmid with Age1 and Not1. The overhangs may then be filled in by blunt end ligation to yield the EYFP1 gene having at its 5' end the junctional sequence corresponding to SEQ ID NO: 7 and having at its 3' end the junctional sequence corresponding to SEQ. ID 8. This fragment may then be inserted into the digested, blunt end plasmid Gfa2 by blunt end ligation to form a plasmid in which the DNA encoding SEQ ID NO: 1 is contiguous with the DNA encoding SEQ ID NO: 7 and in which the DNA encoding SEQ ID NO: 8 is contiguous with the DNA encoding SEQ ID NO: 2 as shown in FIG. 1C. A vector for injection into a mouse zygote may then be prepared by digesting the ligated plasmid with a suitable restriction enzyme.

Methods for producing transgenic animals are known in the art. Transgenic mice may be produced by pronuclear injection as disclosed in U.S. Pat. Nos. 4,736,866, 5,625,125, 5,489,742, 5,583,009, 5,573,933 and 4,873,191, incorporated herein by reference. Transgenic animals, especially mice, may also be produced by homologous recombination or gene targeting in stem cells as disclosed in U.S. Pat. Nos. 5,614,396, 5,416,260 and 5,413,923, incorporated herein by reference.

The morphology of GFP-labeled astrocytes generally resembles that revealed by immunostaining for GFAP. Cell bodies are brightly fluorescent, as are proximal processes and end-feet extending to contact blood vessel walls. However, we calculate that the limit of resolution with our optical settings is on the order of 0.7 $\mu$m, and fine astrocytic processes less than 1 $\mu$m cannot be seen with current techniques. Visualization of such fine processes may require the development of GFPs with higher emission intensities than the mutants used here, or perhaps modifications to direct intracellular trafficking of the GFP protein to the cell surface using membrane targeting signals [Moriyoshi et al., Neuron 16, 255 (1996)].

One of the major applications for these GFAP-GFP transgenic mice is in visualizing dynamic changes in astrocyte morphology, since fluorescence microscopy can be carried out on living preparations. Various changes in astrocyte morphology have been described under different conditions, ranging from coarse changes observable at the light microscopic level as in [Garcia-Segura et al., Glia 10, 59 (1994); Bobak et al., Neurol. 376, 188 (1996)], to much finer changes at the ultrastructural level around synapses after long-term potentiation (LTP) [Wenzel et al., Brain Res. 560, 122 (1991)]. GFP-labeled astrocytes permit study of these alterations in real time, on individual identified cells subjected to various physiological stimuli. In LTP, dynamic changes in length and orientation of neuronal dendritic spines have also been described [Hosokawa et al., J. Neurosci. 15, 5560 (1995)]. Given the appropriate combination of glial and neuronal promoters, and the recent development of fluorescent proteins with novel spectral properties [Zernicka-Goetz et al., Development 122, 3719 (1996); Muldoon et al., BioTechniques 22, 162 (1997)] allowing triple labeling and fluorescence resonance energy transfer, it is now be possible to study the changing relationships between different cell types during both normal and pathological conditions.

The fluorescent signal generated by the GFP in the mice of the present invention is strong enough that it is readily visible in at least two sites amenable to imaging of live animals, the retina and cornea. The retina is an extension of the central nervous system, and contains astrocytes in the nerve fiber layer and the astrocyte-like Mueller cells that span all retinal layers. The astrocytes constitutively express GFAP and up-regulate its expression following injury, whereas the Mueller cells express GFAP only when reactive. Applicant's published studies document the ability to use the GFP as a biomarker of reactivity in living Mueller cells responding to photoreceptor degeneration, in whole mount preparations viewed by confocal microscopy. Recent studies by Sabel et al., Nature Med. 3, 244 (1997), demonstrate that minor modifications to the optics of a standard confocal microscope allowed visualization, in a living rat, of retinal neurons that were labeled with fluorescent markers by retrograde transport. This instrumentation could be adapted to the smaller eye of a mouse, thus allowing monitoring of the GFP signal from retinal astrocytes in living animals.

The cornea is an epithelial surface that is highly innervated by sensory nerve fibers from the trigeminal nerve. As these nerve fibers pass through the corneal stroma, a structure that accounts for most of the corneal thickness, the fibers are ensheathed by non-myelinating Schwann cells. Our unpublished studies indicate that the GFP transgene is expressed in non-myelinating Schwann cells in several sites of the peripheral nervous system, including the cornea. In addition, the GFP signal appeared to increase within 24 hours following traumatic injury to the corneal epithelium. Slit-lamp confocal microscopes suitable for imaging the cornea in clinical settings for humans have been developed [Cavanagh et al., Ophthalmology 100, 1444 (1993)]. As described above for visualizing the retina itself in live animals, minor modifications to such slit-lamp microscopes would allow application to small rodents such as the mouse. Others have used conventional fluorescent microscopes for visualizing sensory nerves of living mice, using non-specific dyes such as 4-D-2-ASP that simply outline structure but provide no information on gene expression [Harris et al. J. Neurosci. 9, 2210 (1989)].

The retina and cornea are appealing sites as they are accessible with a minimum of intervening tissue. The cornea has long been used to test potential toxicity of ophthalmic medications, for obvious reasons, but also as a model for general cutaneous toxicity of any substance that would be applied to or might inadvertently come into contact with the skin. Therefore, the retinal and corneal glia serve as novel sites for evaluating CNS toxicity, due to the relative accessibility for epifluorescent and confocal microscopes, as described above. This may be limited, by definition, to substances that affect the retina. However, advances in other types of optics have led to the development of non-invasive imaging methods for internal organs based on expression of the firefly luciferase gene [Benaron et al., *Biological Sciences* 352, 755 (1997)]. For instance, transgenics expressing the luciferase gene under the control of the inducible LTR from the HIV virus allowed visualization of the luciferase in several tissues, including intestine.

In vivo neurotoxicity of substances may be assayed by other methods as well. For example, the transgenic mice may be exposed to neurotoxic substances at a predetermined dosages for predetermined periods of time. The mice may then be sacrificed and sections from the central nervous system may be analyzed by epifluorescent microscopy, confocal microscopy or fluorometry as described in the examples. Methods of quantitating the fluorescent signals generated by these assays are well known. It is preferable that these results be compared to sections obtained from negative control mice which have not been exposed to the neurotoxin. Mice exposed to the neurotoxin will exhibit an increased fluorescent signal in their astrocytes as compared to the control mice.

EXAMPLES

Materials and Methods
Transgene Construction and Transgenic Mouse Production.

The plasmid Gfa2-lac2 containing the human GFAP promoter and mouse protamine 1 intron and polyadenylation signal on the 3' end was kindly provided by Dr. M. Brenner of the NIH. The plasmid phGFP-SG5T containing the mutated, humanized GFP cDNA was purchased from the Clontech Laboratories. The transgene was constructed by excising the lacZ coding region from the pGfa2-lac2 plasmid by BamHI digestion, and replacing it by blunt end ligation with a 0.75-kb HindIII-XbaI fragment containing the entire GFP coding region from phGFP-S65T (FIG. 1A). The fragment for microinjection was excised using BglII, separated by agarose gel electrophoresis, and purified by glass beads (Bio 101).

Transgenic mice were generated by pronuclear microinjection using fertilized eggs of the FVB/N strain (Taconic). Founder mice were identified by PCR analysis of DNA prepared from tail biopsies collected at weaning, using as the 5' primer GFAP-LZ1 (ACT CCT TCA TAA AGC CCT CG (SEQ ID NO: 9)) and the 3' primer GFP-2 (AAG TCG ATG CCC TTC AGC TC SEQ ID NO: 10)), which are complementary to the GFAP and the GFP-S65T sequences, respectively. The PCR reaction was carried out in a volume of 50 µl containing 0.1 µg genomic DNA in 1× reaction buffer supplemented with 0.1 mM dNTPs, 1.5 MM $MgCl_2$, 600 nm of each primer, and 1.25 units of DNA Taq polymerase. Each of the 35 PCR cycles consisted of denaturation at 95° C. for 1 min., annealing at 60° C. for 2 min., extension at 72° C. for 1 min., and with a final extension for 5 min. The expected size of the PCR product is 498 base pairs.
Northern Blot.

Total RNA was isolated from whole brain of 3-month-old transgenic and nontransgenic mice according to the method of Chomczynski et al., *Anal. Biochem.* 162, 156 (1987). Approximately 20 µg of total RNA per lane was separated on a 1% agarose gel containing formaldehyde, blotted on the UV Duron membrane (Stratagene), and immobilized by using the UV Stratalinker 1800 (Stratagene). A 750-pb GFP-S6ST cDNA fragment, labeled with [α-$^{32}$P]dCTP (Amersham) by random priming (Boehringer Mannheim), was used to probe the RNA blot in "Rapid-hyb" hybridization buffer (Amersham) with approximately $10^6$ cpm/ml at 65° C. for 2 hr. The blot was washed in 0.1×SSC and 0.1% SDS at 65° C. for 2 hr., and then exposed to X-ray film with an intensifying screen at −70° C. for 2 days.
Tissue Preparation and Laser Confocal Microscopy.

Hemizygous transgenic mice, ranging in age from 5 weeks to 4.5 months, were used for confocal analyses. Nontransgenic littermates (age- and sex-matched) were used as negative controls. Tissues subjected to examination included the brain (cerebellum, hippocampus, cerebral cortex, hypothalamus), optic nerve, retina, sciatic nerve, vagus nerve, diaphragm, heart, kidney, liver, lung, and pancreas. Vibratome slices of 300 µm thickness, or whole mounts of intact nerves or retina, were mounted in a perfusion chamber supplied with Ringer's physiological solution at room temperature for live observation. Tissue samples were analyzed using either an Odyssey confocal laser scanning microscope system (Noran Instruments) or an MRC-1024 (Bio-Rad). For GFP imaging, filters were employed to provide excitation at 488 nm, detecting emission at wavelengths greater than 515 nm. A 4× (Olympus, NA=0.1) or 40× (Olympus, NA=0.7) water-immersion objective was used to view intact nerves or tissue slices, respectively. Each image was formed by averaging 16–256 frames using MetaMorph software (Universal Imaging). The GFP could also be viewed using an ordinary epifluorescence microscope equipped with a filter set for fluorescein.
GFAP/GFP Double Imaging in Vibratome Sections.

Transgenic and nontransgenic mice were perfused with 4% paraformaldehyde in PBS (pH 7.4), and then the brains were removed and postfixed in the same fixative for an additional 4 hr. at 4° C. Vibratome sections (40 µm in thickness) of brain regions were cut in cold PBS, and incubated for 4–12 hr. at 4° C. in PBS containing 0.1% (v/v) Triton X-100 and 10% nonimmune goat serum. Sections were then washed 5×15 min. in PBS and incubated for 24 hr. at 4° C. with a rabbit anti-bovine GFAP polyclonal antibody (Dako) at 1:500 dilution in PBS containing 0.01% Triton X-100 and 1% nonimmune goat serum. The sections were again washed with 5×15 min. in PBS and then incubated 4–8 hr. at room temperature with rhodamine-conjugated goat anti-rabbit IgG antiserum (Sigma) at 1:80 dilution in PBS containing 0.01% Triton X-100 and 1% nonimmune goat serum. The sections were then rinsed in four changes of PBS, and transferred to slides and coverslipped in 50% glycerol in PBS. GFAP immunofluorescence and GFP fluorescence were visualized in the same sections, using standard rhodamine and fluorescein filters, respectively, with ordinary wide-field epifluorescence and with confocal laser scanning microscopy.

EXAMPLE 1

Generation of Transgenic Mice

In pilot experiments, transgenic mice were generated carrying the wild-type GFP under the control of the hGFAP promoter. Confocal imaging of brain slices from expressing lines of mice revealed only weakly fluorescent cells, and these lines of mice were not further analyzed. We subsequently tried a variant of GFP with codons altered to be more optimal for expression in mammalian cells ("humanized," or hGFP), and an S65T mutation that changes the excitation spectrum and increases fluorescence intensity (Heim et al., 1995). Using the hGFP-S65T mutant, nine transgenic founder mice were obtained, and all successfully transmitted the transgene to their offspring to establish breeding lines. Expression of the transgene was initially evaluated at the mRNA level by Northern blot analysis of brains collected from offspring in each line (FIG. 1B). Three lines displayed a 1.3-kb transcript in brain, and the two strongest expressing lines (Tg94.4 and Tg94.7) were expanded for further analysis. The transgenic mice in both lines developed normally into adulthood and were fertile, indicating no deleterious effects of transgene expression. As described in sections below, these two lines had the same expression pattern in all the tissues examined.

EXAMPLE 2

Tissue Autofluorescence and Confocal Settings

We surveyed eight live tissues, under identical imaging conditions, from an adult FVB mouse (300-$\mu$m-thick vibratome sections) for autofluorescence overlapping the GFP emission band. Autofluorescence was found in every mouse tissue examined, transgenic and nontransgenic alike. Strong autofluorescence would present a formidable obstacle to using GFP. Fortunately, we found that our particular tissues of interest (CNS and PNS) had lower autofluorescence compared with nonneural tissues, in the following order: CNS (whole brain slice)=PNS (vagus and sciatic nerves)<lung<pancreas<diaphragm<kidney<heart<liver. In addition, autofluorescence was higher in dead or fixed tissues. Based on these observations, we used tissues from nontransgenic littermates as a reference to set an appropriate baseline for confocal imaging, and at the same time took precautions to keep tissues alive during the imaging process to minimize autofluorescence.

EXAMPLE 3

GFP Expression in the Optic Nerve

Figure 2A:
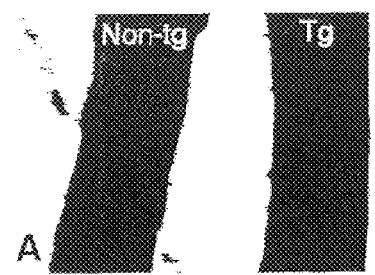
FIG. 2(A) is a bright-field view of optic nerves from a 6-week-old nontransgenic mouse (left) and transgenic mouse (right).
Figure 2B:
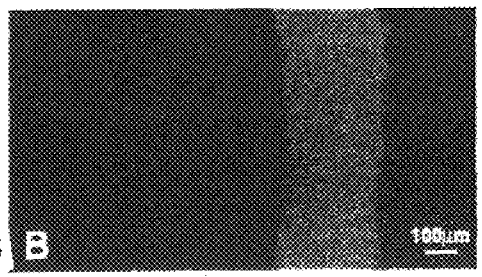
FIG. 2(B) is the same field as 2 A illuminated with a 488-nm laser.
Figure 2C:
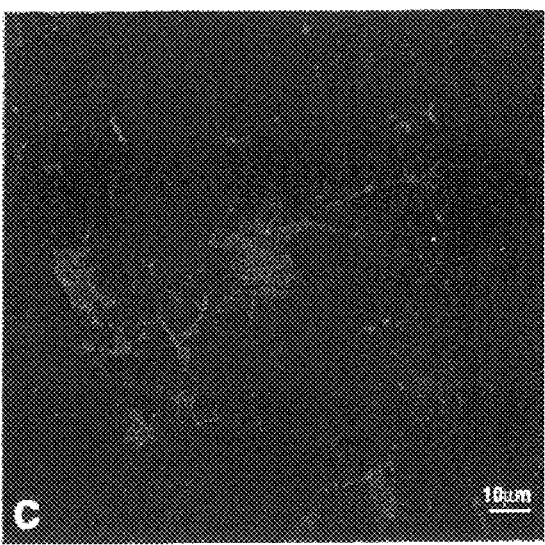
FIG. 2(C) is the transgenic optic nerve shown in 2 B visualized at a higher magnification using a 40×water-immersion lens.

The optic nerve is one of the simplest parts of the CNS, containing primarily cell bodies of astrocytes and oligodendrocytes, and axons of retinal ganglion cells. We first attempted to visualize GFP fluorescence at low magnification. Using a simple light transmission mode, whole-mounted optic nerves from two littermates (one transgenic and the other nontransgenic) appeared as dark trunks (FIG. 2A). However, when the same field was illuminated with laser, the transgenic nerve emitted strong diffuse fluorescence, whereas the nontransgenic nerve showed no signal (FIG. 2B). At higher magnification (using a 40×water-immersion objective), individual cells could be visualized with the typical morphology of astrocytes (FIG. 2C).

EXAMPLE 4

GFP Expression in the Brain

Figure 3A:
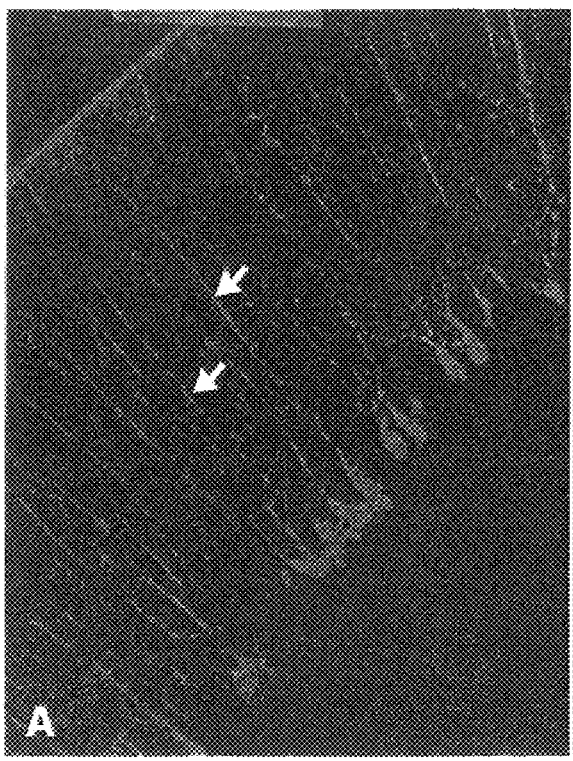
FIG. 3(A) is a brain vibratome section viewed with laser excitation for GFP expression.
Figure 3B:
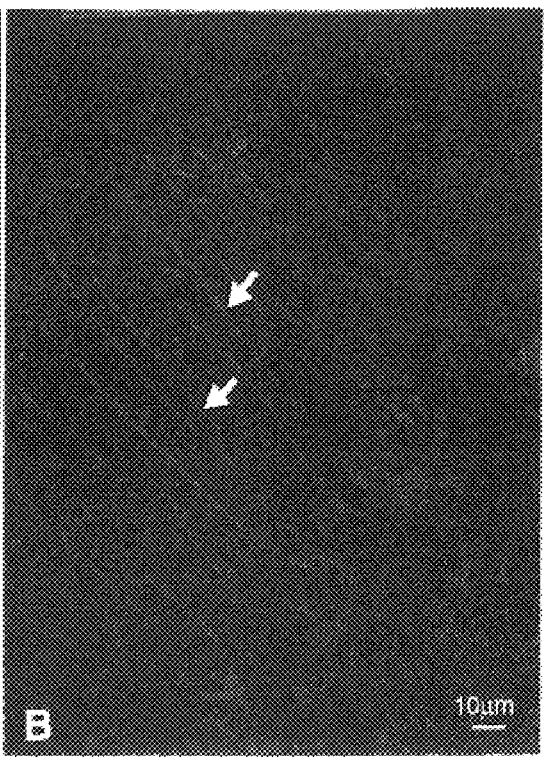
FIG. 3(B) is the same section as in 3(A) labelled with a GFAP antibody and detected via a rhodamine-conjugated secondary antibody.

Another site in the central nervous system where astrocyte morphology is so distinctive as to be unambiguous is in the cerebellar cortex, where Bergmann glia have their cell bodies adjacent to large Purkinje cell neurons and send radial processes out to the pial surface. In vibratome sections of transgenic cerebellum, the Bergmann glia were strongly fluorescent (FIG. 3A). To verify that GFP-expressing cells were indeed astrocytes, we performed immunofluorescent staining of the same sections for GFAP, the astrocyte-specific intermediate filament whose promoter was used to direct expression of the GFP. Since GFP emits with spectra resembling FITC, we used a rhodamine-conjugated secondary antibody to detect the GFAP (FIG. 3B). All of the GFP-labeled cells were also labeled for GFAP (examples of dual-labeled radial fibers are indicated by arrows in both photographs), although not all astrocytes expressed detectable levels of GFP (for instance, in the granule cell layer). The GFP signal was very prominent in the Bergmann glial cell bodies, where GFAP labeling is typically low [Ludwin et al., *J. Comp. Neurol.* 165, 197 (1976)]. The large cell bodies of the Purkinje cells displayed no visible fluorescence, appearing as dark holes next to the Bergmann glia. GFP-expressing astrocytes were observed throughout the CNS, including hippocampus, hypothalamus, and cerebral cortex. Neurons in all of these sites were unlabeled.

EXAMPLE 5

GFP Expression in the Retina

The retina contains two major glial cell types, the astrocytes located in the ganglion cell layer (GCL) near the retinal surface and the Mueller cells with cell bodies in the inner nuclear layer (INL) and processes extending radically through the other retinal layers. Like their counterparts elsewhere in the CNS, astrocytes in the retinal ganglion cell layer express GFAP. However, Mueller cells only express GFAP when reactive, as a response to various forms of retinal disease [Sarthy et al., *DNA* 8, 437 (1989); Erickson et al., *J. Struct. Biol.* 108, 148 (1992)]. We initially examined expression of the GFP transgene in normal retinae with nonreactive Mueller cells by crossing the parent GFP transgenics (which were on the inbred FVB/N background that is homozygous for the rd mutation) with C57Bl/6J mice which are +/+ at the rd locus. F1 offspring from such crosses are therefore heterozygous for rd and have intact photoreceptors.

Figure 4A:
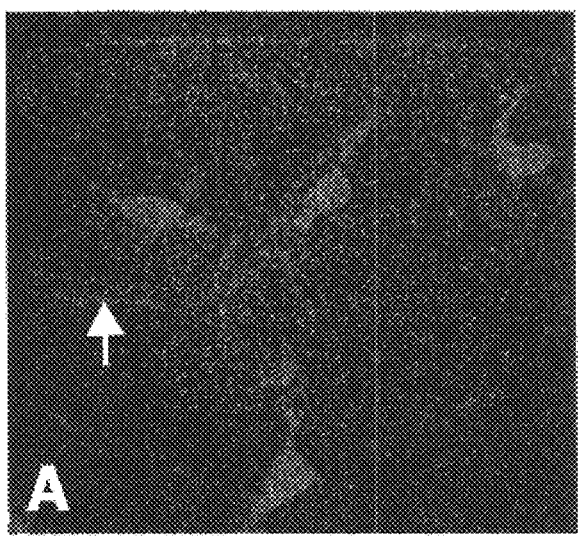
FIG. 4(A) is retinal whole-mount preparation from a 6-week-old transgenic female on the hybrid B6 X FVB/N background, visualized for GFP in the plane of the ganglion cell layer.

A series of confocal images were taken vertically from a retinal whole mount flattened with agar in a perfusion chamber. At the surface, the large, brightly fluorescent astrocytes of the ganglion cell layer extended processes laterally that made extensive contacts with blood vessels (FIG. 4A). There was no evident fluorescence in the endfeet of Mueller cells or in any other cell types. Images from the deeper inner nuclear cell layer also confirmed the absence of transgene expression in the Mueller cells. As negative controls, no fluorescent signal was detected in nontransgenic retina (data not shown).

Figure 4B:
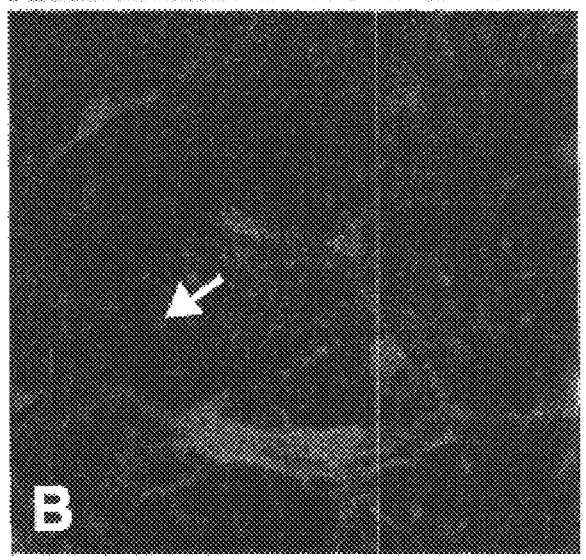
FIG. 4(B) is retinal whole-mount preparation from a 6-week-old transgenic female on the inbred FVB/N background, visualized for GFP in the plane of the ganglion cell layer.
Figure 4C:
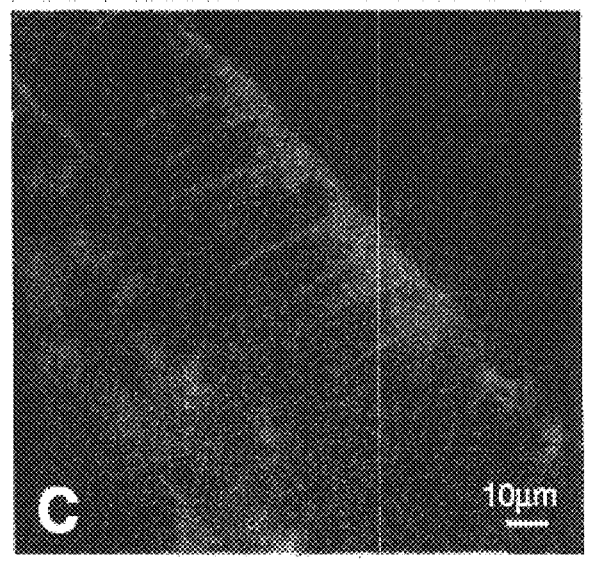
FIG. 4(C) shows a transverse section of a retina taken from a 4.5 month old transgenic male (Tg94.7) on the FBV/N background, visualized for GFP.
Figure 5:
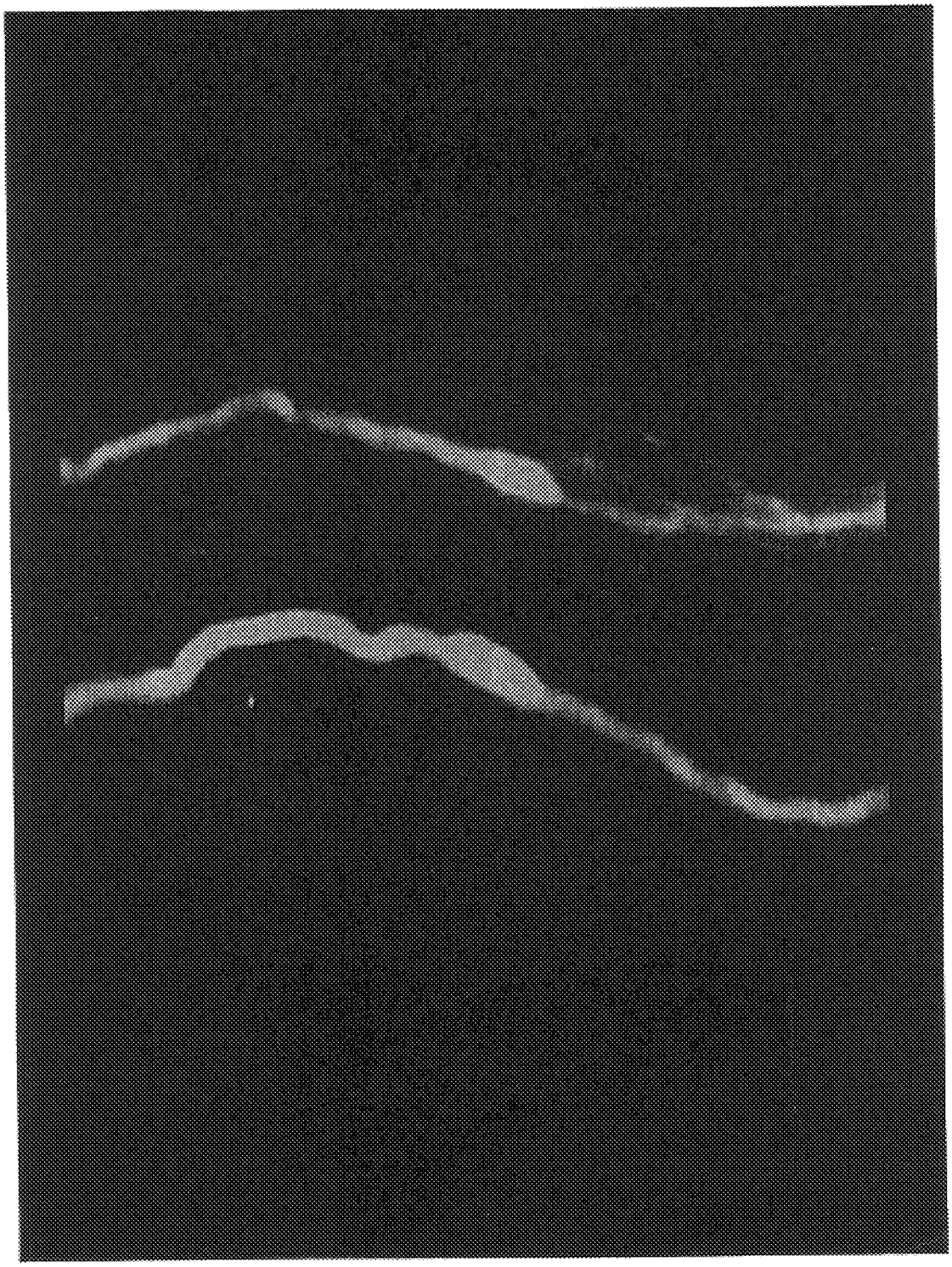
FIG. 5 is a confocal micrograph demonstrating that living non-myelinating Schwann cells in sciatic nerve express GFP (40× lens).
Figure 6:
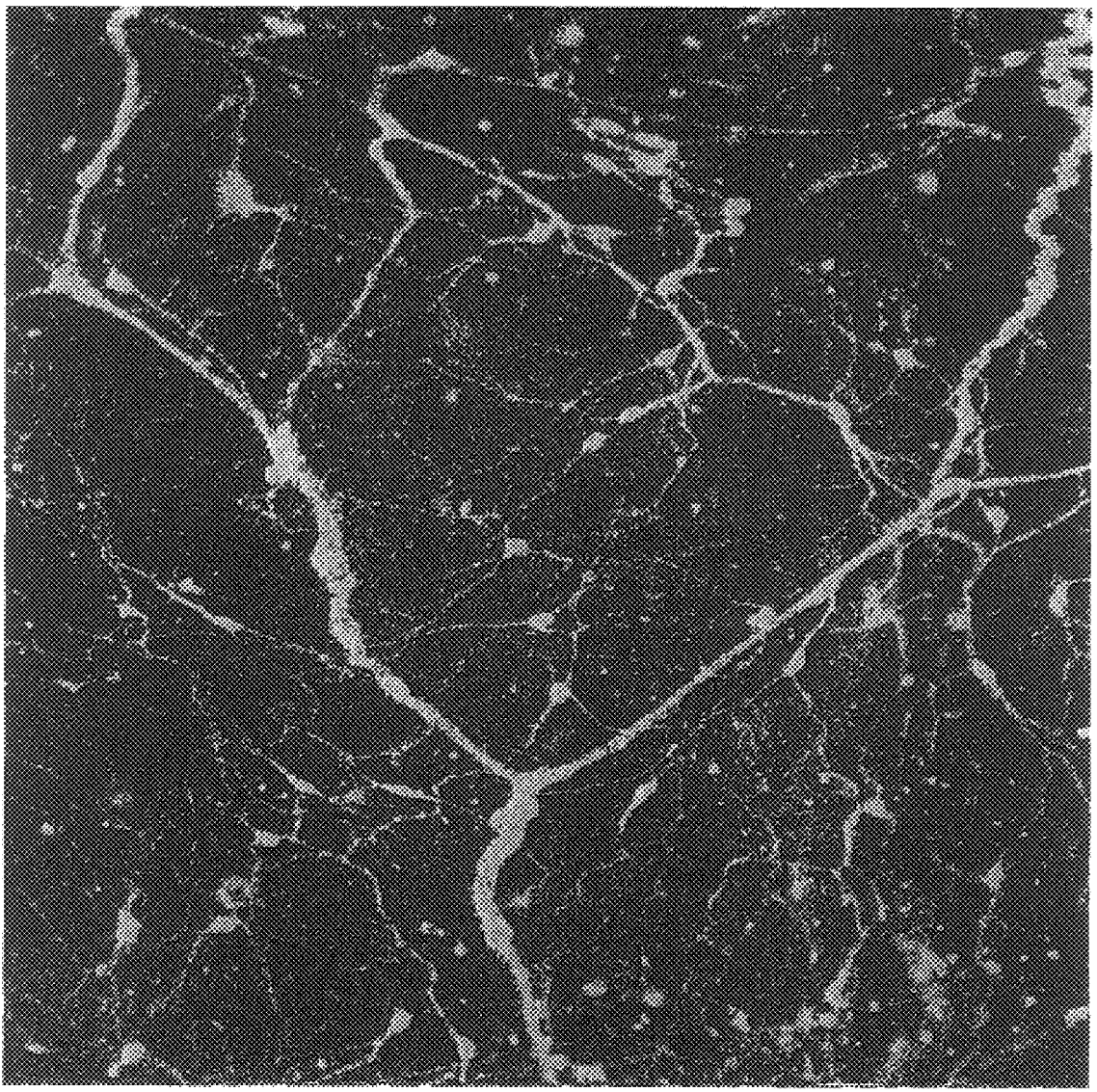
FIG. 6 is a confocal micrograph showing non-myelinating Schwann cells labeled by GFP in transgenic cornea (20× lens).
Figure 7A:
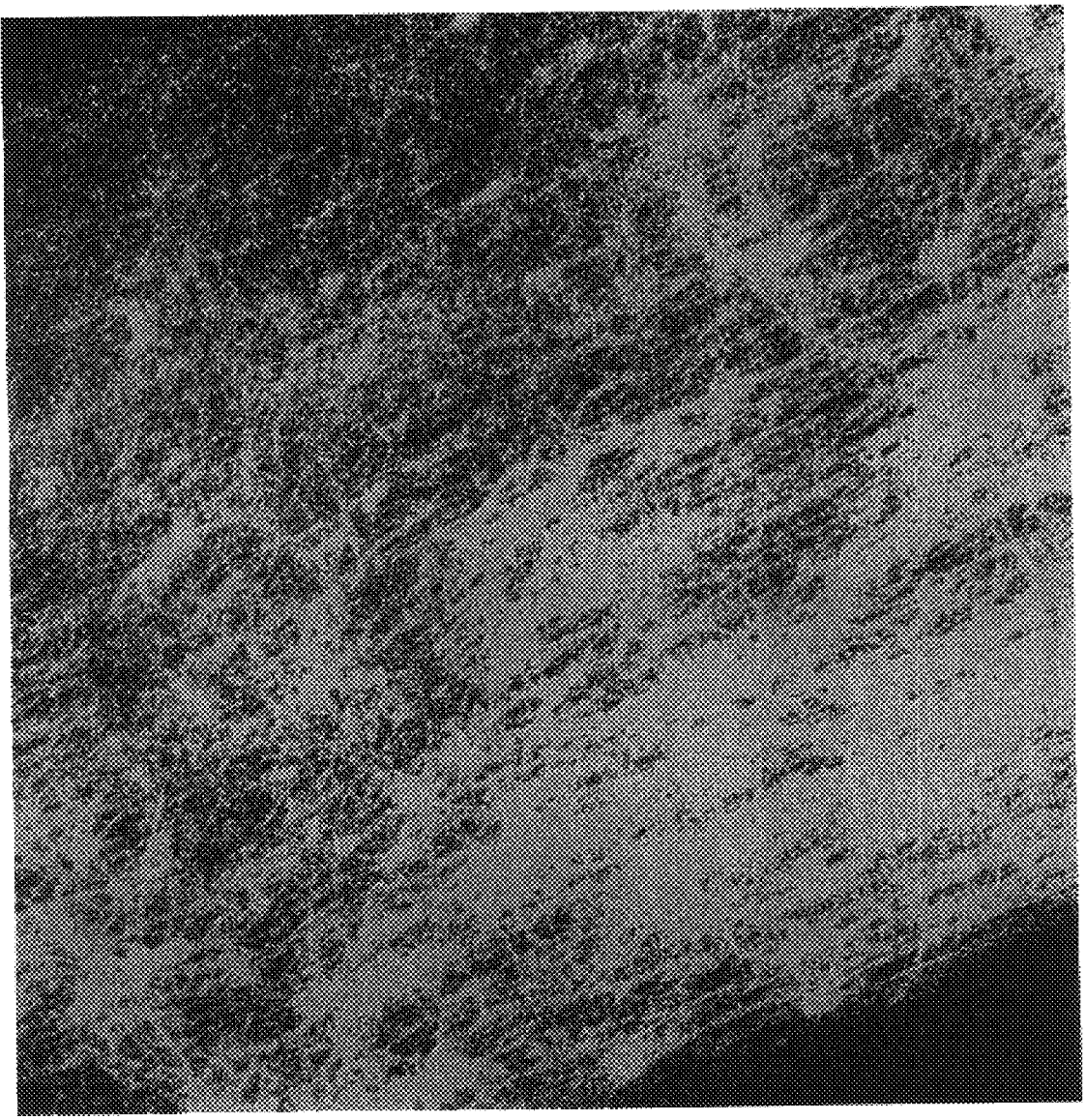
FIGS. 7A and 7B are confocal micrographs demonstrating the GFP intensity difference between injured nerve and non-injured nerve.
Figure 7B:
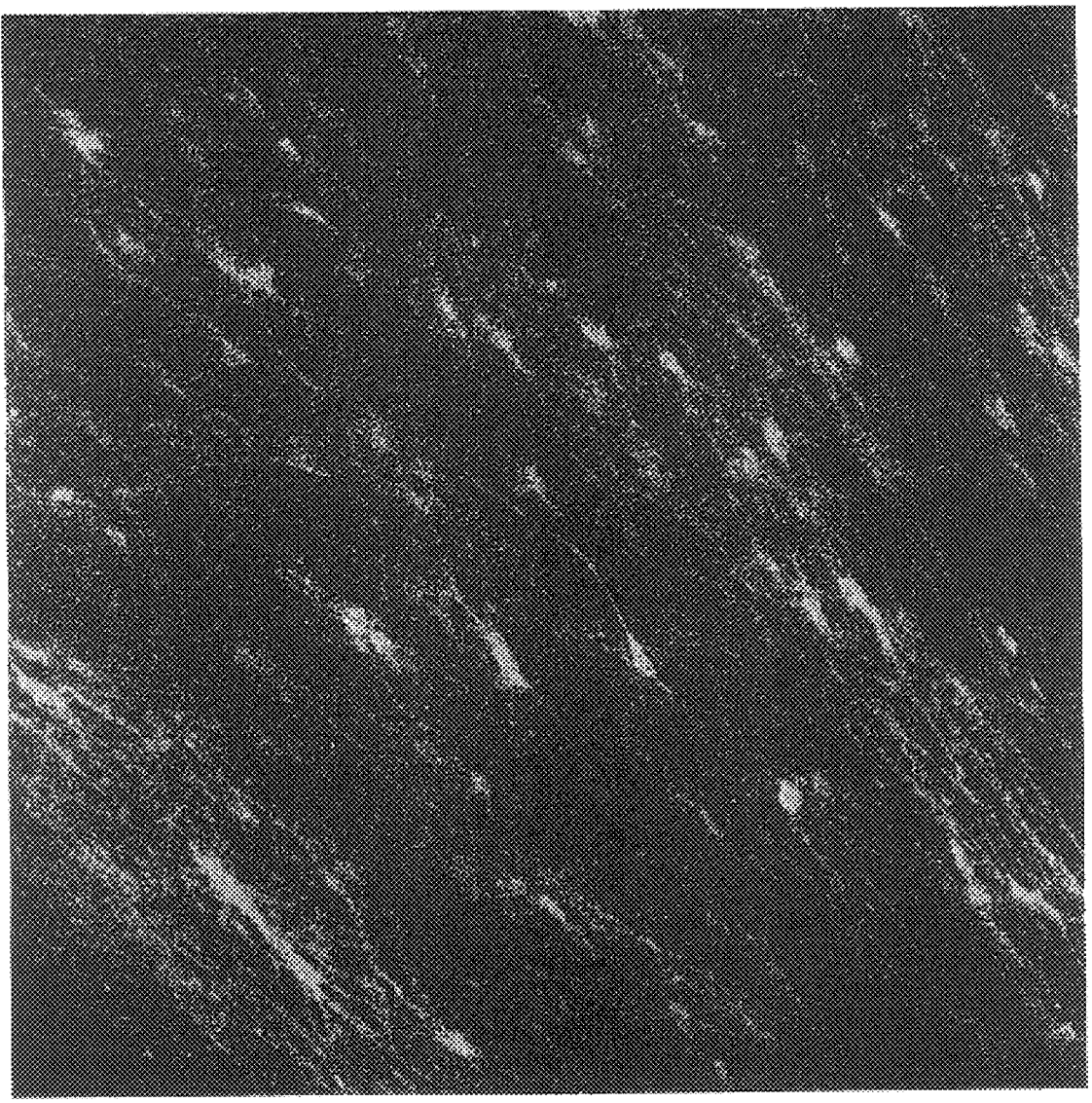
Figure 8A:
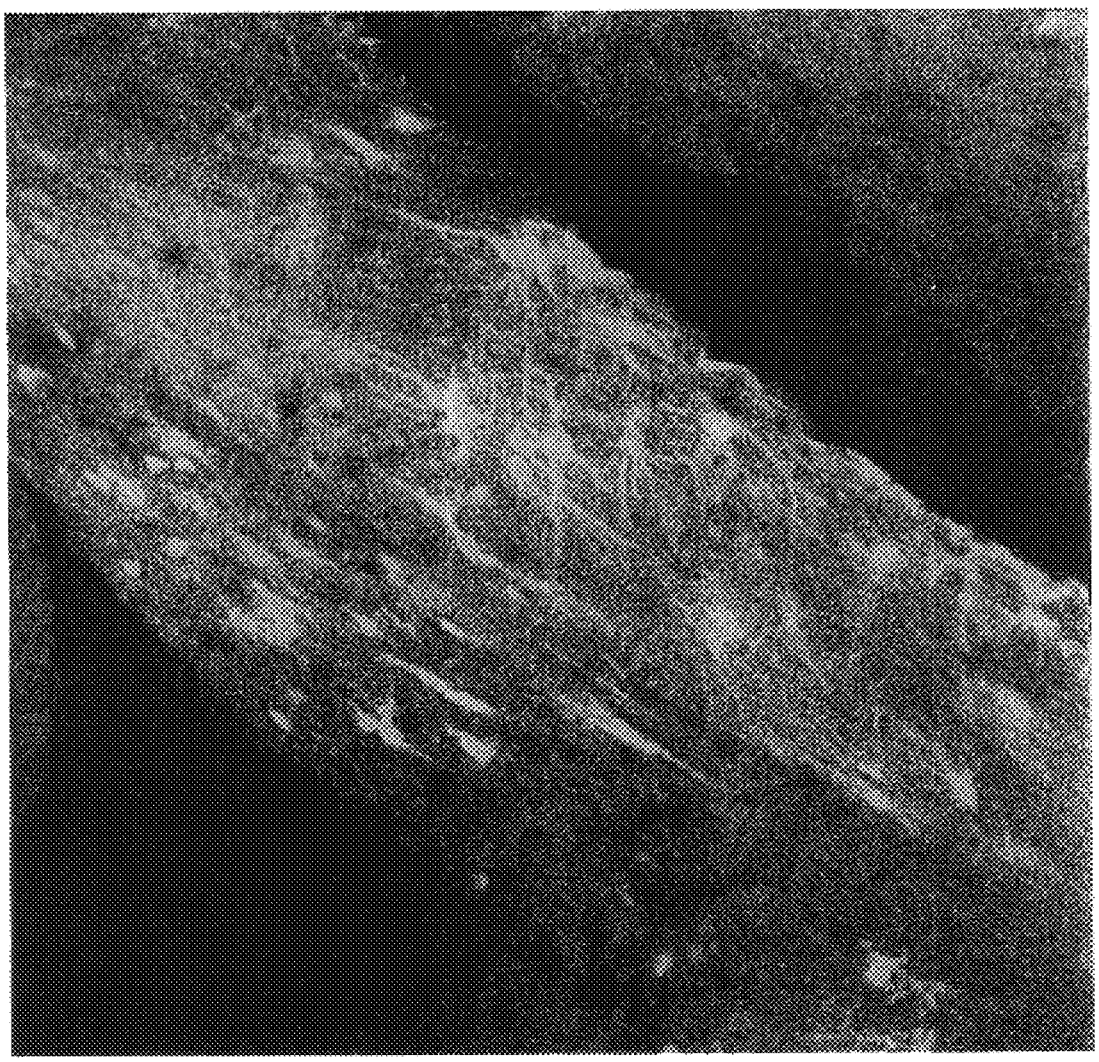
FIGS. 8A and 8B are confocal micrographs of optic nerve from a Jimpy X GFAP-GFP mouse and a plain GFAP-GFP mouse.
Figure 8B:

We next evaluated GFP transgene expression in the retina of mice on the inbred FVB/N background. As a consequence of the photoreceptor degeneration caused by the rd mutation, Mueller cells in adult FVB/N mice are spontaneously reactive and express GFAP. A similar series of confocal images were taken from whole-mounted retina as described above. Once again, astrocytes of the ganglion cell layer were clearly seen contacting blood vessels (FIG. 4B). In addition, however, interspersed between astrocytes of the ganglion cell layer were numerous small foci of fluorescence (FIG. 4B). A transverse section through another transgenic retina (pure FVB/N background) revealed the presence of brightly fluorescent cell bodies in the inner nuclear layer with radial processes extending up to the vitreal surface, the hallmark features of Mueller cells (FIG. 4C). The GFP transgene is thus appropriately regulated in retinal Mueller cells.

EXAMPLE 6

Method for Quantifying GFP Signal in Tissue Slices or Live Tissue

Images of tissue slices or living tissue are captured on computer using standard confocal microscopes and image analysis software such as MetaMorph. To quantitate the fluorescent signal, an area of the image is selected (which, depending on magnification, may be at the level of individual cells up through broad areas of tissues) and the average pixel value is calculated by the software. Areas of the slide that do not contain tissue, or have tissue from a non-transgenic mouse, can be used to calculate background which can be subtracted automatically from the signal if desired.

EXAMPLE 7

Non-myelinating Schwann Cells in the Sciatic Nerve

Sciatic nerve from a 6-week-old transgenic mouse was mounted in a perfusion chamber supplied with Ringer's physiological solution at room temperature for live observation. Nerve was imaged by using an Odyssey confocal laser scanning microscope (Noran Instruments) with a 40 k water-immersion objective. Filters were employed to provide excitation at 488 nm, detecting emission at wavelengths at 515 nm. Each image was formed by averaging 16–256 frames using MetaMorph 2.5 software (Universal Imaging Corp.).

Bipolar cells oriented longitudinally within the nerve trunks were clearly visible by fluorescence microscopy. The identity of GFP-expressing cells as non-myelinating Schwann cells was confirmed by double labeling them by immunocytochemistry for GFAP, using the same methods as previously reported for the cerebellum (Zhuo et al., supra).

EXAMPLE 8

Non-myelinating Schwann Cells in Cornea

Freshly dissected corneas from adult transgenic and non-transgenic mice were mounted on a glass slide in PBS and sealed with nail polish for immediate imaging. Alternatively, tissues could be fixed in 10% formalin on ice for delayed imaging. Mounted samples were imaged with an MCR-1024 confocal microscope (Bio-Rad) with 20× objective. The excitation and collection wave lengths are routinely 488 and 510 nm respectively.

GFP-expressing cells were detected in the cornea with the morphological characteristics consistent with non-myelinating Schwann cells. The GFP intensity in NMSC is comparable to that in retinal Mueller cells. No cell was labeled by GFP in non-transgenic cornea. GFP signal intensity was significantly elevated 24 hours post injury (scraping the corneal epithelium).

EXAMPLE 9

Optic Nerve Transection

Enucleation was performed on adult transgenic mice to effect transection of the optic nerve and induce wallerian degeneration in the intracranial portion of the nerve. Four days after injury the injured (left) and intact (right) optic nerves of the same mouse were isolated and fixed in 10% formalin for two hours. The middle portion of the fixed nerves were then mounted side by side on a glass slide for imaging. The same set of confocal parameters were used to image both the injured and the non-injured nerves.

The transgene responds to mechanical injury to optic nerve by significantly increasing GFP production at day 4 post injury. We have not yet tested earlier time points.

EXAMPLE 10

GFAP-GFP Expression in Jimpy Mutant Mice

The GFAP-GFP transgene also responds to myelin defect exhibited by Jimpy mutants. Astrocytes in these mice have hypertrophic astrocytes with increased GFP signal intensity. The GFP increase in this case was qualitatively larger than that seen for optic nerve transection at day 4.

Optic nerves were isolated from GFAP-GFP transgenics, some of which also carried the Jimpy mutation. This mutation occurs in the PLP gene, which lies on the X-chromosome. Affected males develop hypomyelination in the CNS and typically die by 3 weeks postnatal with prominent gliosis and up-regulation of GFAP. For this comparison we evaluated mice at 2 weeks postnatal.

EXAMPLE 11

GFP Solution Assay

GFP expression can also be quantitated in extracts by fluorometry. Brain from adult transgenic and non-transgenic mice were homogenized in ice-cold PBS. After centrifugation at 1500 g for 5 minutes, supernatant was collected for total protein quantitation using the BCA (Bicinchoninic Acid) kit (Sigma Chemicals). Fluorescence of the supernatant was measured using a Shimadzu fluorometer (Shimadzu, Japan) with excitation at 488 nm, and collection at 510 nm.

GFP fluorescent intensity (FI) from the transgenic extracts is 202% of the auto-fluorescent intensity from the non-transgenic extracts. The linear correlation coefficients for both transgenic and non-transgenic FI measurements reach 0.99, for total protein concentrations ranging from 0.2 to 5 mg/ml. The solution assay also accurately quantitated the GFP signal differences observed at both the mRNA and confocal image levels between transgenic lines 94-7 and 94-4, with the former being 125% of the later.

What is claimed is:

1. A transgenic mouse comprising in its genome a gene encoding a green fluorescent protein operably linked to a glial fibrillary acidic protein promoter, wherein the green fluorescent protein is expressed in Mueller cells.

2. A method of determining the neurotoxicity of a substance comprising
   (a) providing a first transgenic mouse and a second transgenic mouse, both according to claim 1;
   (b) exposing the first transgenic mouse to the substance;
   (c) visualizing green fluorescence signal of the glial cells of the first and second transgenic mice; and
   (d) comparing the green fluorescence signal of the glial cells of the first and second mice mouse obtained in step (c), wherein an increase in the green fluorescence signal in the glial cells of the first transgenic mouse as compared to the signal in the glial cells of the second mouse indicates that the substance is neurotoxic.

3. A method of screening a substance for neurotoxicity comprising the steps of:
   (a) providing a transgenic mouse according to claim 1;
   (b) visualizing the green fluorescence signal of the glial cells of the transgenic mouse;
   (c) exposing the mouse to the substance;
   (d) visualizing the green fluorescence signal in the glial cells of the transgenic mouse after step (c); and
   (e) comparing the fluorescence signals obtained in steps (b) and (d), wherein an increase in the fluorescence signal of step (d) as compared to step (b) indicates that the substance is neurotoxic.

* * * * *